United States Patent [19]

Liu

[11] Patent Number: 4,584,992

[45] Date of Patent: Apr. 29, 1986

[54] STEAM-HEATING BREAST MASSAGER

[76] Inventor: Su-Hwa Liu, No. 41-2 Hsin Kwang Road, Kaohsiung, Taiwan

[21] Appl. No.: 557,835

[22] Filed: Dec. 5, 1983

[51] Int. Cl.4 ........................ A61H 29/00; A61F 7/00

[52] U.S. Cl. .................................... 128/24.1; 128/402

[58] Field of Search .............. 128/399, 400, 402, 24.1, 128/67, 367, 368; 137/624.14; 604/312, 313

[56] References Cited

U.S. PATENT DOCUMENTS

| | | | |
|---|---|---|---|
| 1,177,388 | 3/1916 | Crane | 128/24.1 X |
| 2,222,811 | 11/1940 | Dinesen . | |
| 2,616,417 | 11/1952 | Holbrook | 128/38 |
| 3,037,498 | 6/1962 | Smith | 128/30 |
| 3,382,867 | 5/1968 | Reaves | 128/38 |
| 3,949,743 | 4/1976 | Shanbrom | 128/368 |

*Primary Examiner*—Richard J. Apley
*Assistant Examiner*—Kathleen D'Arrigo
*Attorney, Agent, or Firm*—Holman & Stern

[57] ABSTRACT

This utility is concerned with an improvement in a breast massager equipped with a steam generator and a set of suction generator. The half part of the breast cup of said massager is designed to have double walls separated between and the space surrounded by said walls forms a vapor room. The internal wall of said breast cup facing the breast is all over bored with a plurality of vapor holes through which vapor can run. During operation, a set of suction generator, consisting of a vacuum compressor and a on-off electromagnetic valve controlled by an electronic timer, can operate to suck and release the breast through said breast cup and meanwhile the warm vapor produced by a stream generator can flow into the vapor room penetrating through said holes and spreading over and warming the breast. Therefore, the above-mentioned functioning is surely possible to accomplish the breast beautification.

2 Claims, 3 Drawing Figures

STEAM-HEATING BREAST MASSAGER

BACKGROUND OF THE UTILITY

Almost all fair sex care about their physical beauty and endeavour to beautify themselves as much as they can. Ever since a conventional breast massager has come into existence, it goes without saying that female physical figures could be improved more or less through its use. And practically some females may have changed their pessimistic thought about life into happy one after having improved their own figures by means of this massager, no matter what the medical world might have said about this breast massager. It can not be denied that girls desiring for a nice figure have really obtained some effects using the massager.

Nevertheless, the existing breast massager must use in its operation a kind of cream which does not have enough wetness to acquire quick effect desired. This is the defect that this inventor has wanted to improve, and this utility has been worked out in order to bring about happiness for the fair sex.

THE DETAILED DESCRIPTION OF THE UTILITY

Figure 1:
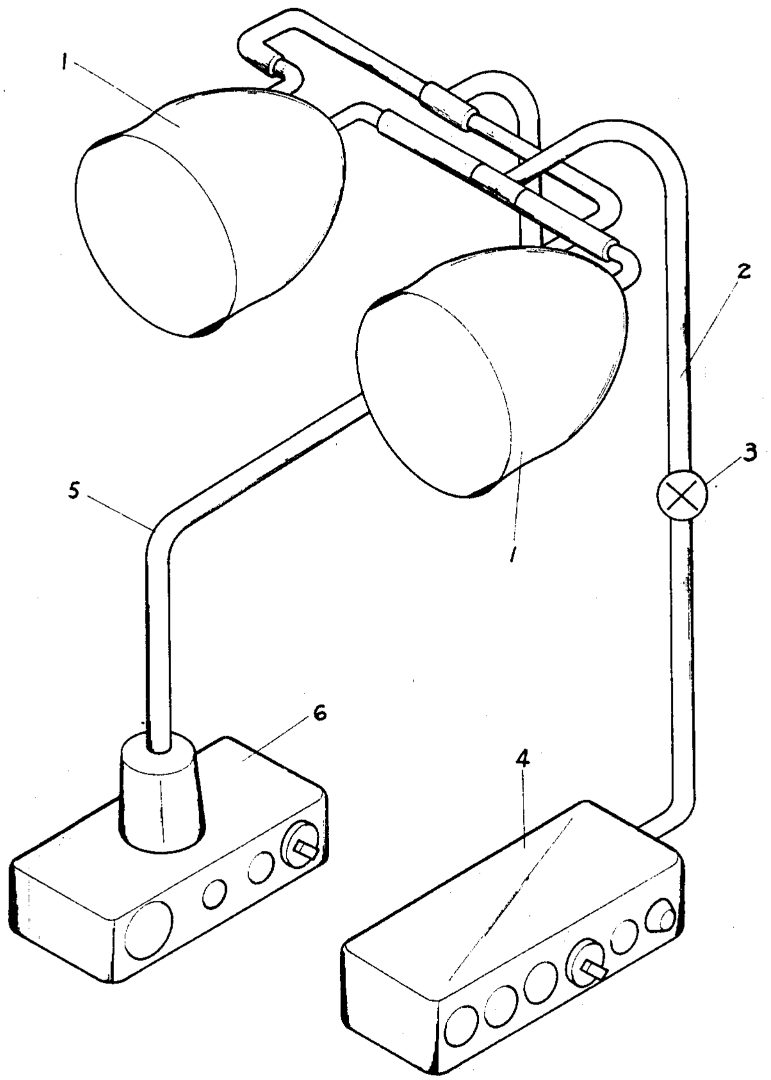
FIG. 1 is the diagram of this breast massager.

As shown in FIG. 1, this breast massager is designed to be equipped with two breast cups 1 connected with suction generator 4 through suction pipe 2 and electromagnetic valve 3. Said suction generator 4 includes an electronic timer controlling the on-off action of said on-off electromagnetic valve 3. Said timer turns on or off the electricity for a period of time previously set—15, 20 or 25 minutes—with the electricity on or off three (or any) seconds alternately. This alternate on-off electricity makes electrmagnetic valve do the same operation. During operation, when said electromagnetic valve is opened (on) the breast covered by said breast cup will be sucked up, but when it is closed (off), the suction is stopped so that the breast will be released. The operation of said timer is quite a common electronic application, which will not be detailed herein.

The shape of said breast cup is designed according to that of the feminine breast. The sucking pressure generated by said generator 4 is led through air pipe 2 to the inside of said breast cup 1, sucking the air out of said cup tightly covered the breast or releasing the air into it-which means the action of massage on the breast.

Figure 2:
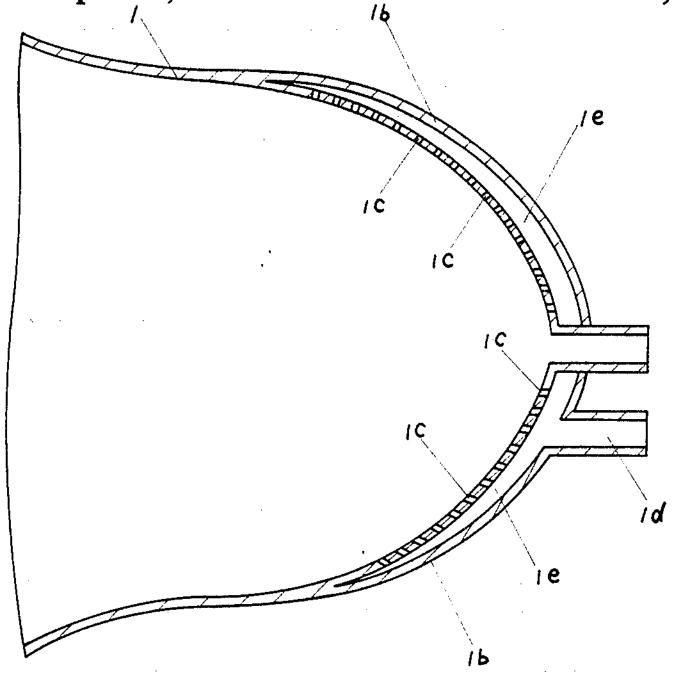
FIG. 2 is the cross-sectional view of the breast cup in this utility.
Figure 3:
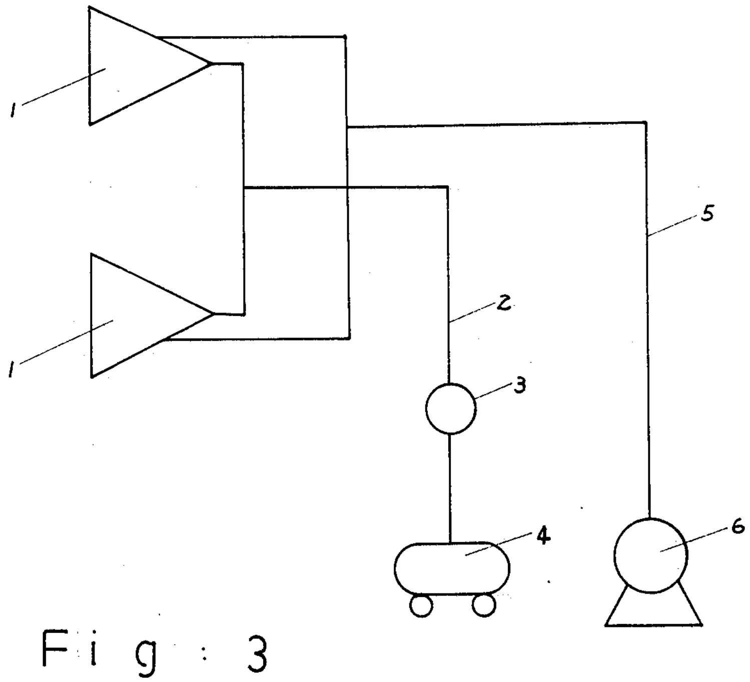
FIG. 3 is the diagram of the air pipe and vapor pipe connected the other parts in this utility.

As shown in FIG. 2, the lower part of said breast cup 1 possesses two layers of walls separated between—internal wall 1*a*, external wall 1*b*. Said internal wall 1*a* is the one facing the breast and a plurality of vapor holes 1*c* are bored all over in it. Said external wall 1*b* is totally closed except that there is a vapor pipe joint 1*d* attached on it to be linked with vapor pipe 5 leading to steam generator 6 which produces vapor by boiling water electrically. Said steam generator 6 is equipped with an electronic timer that can be set to go in coordination with that of massaging action to warm up the breast and to stimulate growing new cells in the breast.

Said vapor room 1*e* is the space where is surrounded by the two walls of the lower part of said breast cup 1. Said room 1*e* is connected through said vapor pipe 5 with said steam generator 6 and also communicates with the interior of said breast cup 1 through the plurality of said vapor holes 1*c*. The vapor, being controlled properly, gives the breast a comfortable feeling of the temperature between 50° C.-60° C. because of its small volume, and wets the breast as well to make massaging easier and more comfortable after penetrating through said holes 1*c* into the inside of said breast cup 1. In the process of repeated sucking and releasing, vapor is pervaded on the breast, making it properly wet and warm so that the breast can get soft and massaged with good and satisfactory results.

What is claimed is:

1. A steam-heating breast massager comprising a pair of breast cups, only a half part of said cups having two separated layers of cup walls forming a space for storing water vapor, said vapor running through a plurality of vapor holes bored in the internal wall of said half part of said breast cups, said breast cups being connected to a suction generator means and to a steam generator means, said suction generator means causing sucking and releasing action massaging the breast, which is simultaneously warmed up and softened directly by the water vapor coming from said steam generator means through said vapor holes, the action of the steam and suction generators being coordinated by a timer means.

2. The breast massager of claim 1 wherein said suction generator comprises a vaccum compressor and an on-off electromagnetic valve controlled by an electronic timer.

* * * * *